US011906725B2

(12) United States Patent
Harada

(10) Patent No.: US 11,906,725 B2
(45) Date of Patent: Feb. 20, 2024

(54) ILLUMINATION LENS, ILLUMINATION OPTICAL SYSTEM, AND ENDOSCOPE

(71) Applicant: FUJIFILM Corporation, Tokyo (JP)

(72) Inventor: Keisuke Harada, Saitama (JP)

(73) Assignee: FUJIFILM Corporation, Tokyo (JP)

(*) Notice: Subject to any disclaimer, the term of this patent is extended or adjusted under 35 U.S.C. 154(b) by 892 days.

(21) Appl. No.: 16/798,439

(22) Filed: Feb. 24, 2020

(65) Prior Publication Data

US 2020/0271915 A1    Aug. 27, 2020

(30) Foreign Application Priority Data

Feb. 27, 2019    (JP) .................................. 2019-034991

(51) Int. Cl.
G02B 23/24    (2006.01)
G02B 9/06    (2006.01)
G02B 3/00    (2006.01)

(52) U.S. Cl.
CPC ............. *G02B 23/243* (2013.01); *G02B 9/06* (2013.01); *G02B 23/2461* (2013.01); *G02B 3/0075* (2013.01); *G02B 2003/0093* (2013.01)

(58) Field of Classification Search
CPC .............. G02B 23/243; G02B 23/2461; G02B 9/04–10; G02B 13/003; G02B 13/005; G02B 19/0023; G02B 19/0047; G02B 19/0052; G02B 19/0061; A61B 1/00096; A61B 1/00163

See application file for complete search history.

(56) References Cited

U.S. PATENT DOCUMENTS

| 5,951,464 | A | * | 9/1999 | Takahashi | .......... | A61B 1/00165 |
| | | | | | | 600/176 |
| 6,134,056 | A | * | 10/2000 | Nakamuka | .......... | G02B 23/243 |
| | | | | | | 600/101 |
| 6,466,536 | B1 | | 10/2002 | Katsuma | | |
| 8,118,734 | B2 | | 2/2012 | Murayama | | |
| 8,647,263 | B2 | * | 2/2014 | Murata | .............. | A61B 1/00096 |
| | | | | | | 600/160 |
| 9,039,605 | B2 | * | 5/2015 | Sone | ...................... | G02B 23/26 |
| | | | | | | 600/117 |

(Continued)

FOREIGN PATENT DOCUMENTS

| CN | 1265745 | 9/2000 |
| CN | 103460111 | 12/2013 |

(Continued)

OTHER PUBLICATIONS

English Machine Translation of JP-2005345787-A (Year: 2005).*
Office Action of China Counterpart Application, with English translation thereof, dated Feb. 28, 2023, pp. 1-19.

*Primary Examiner* — Nicholas R. Pasko
(74) *Attorney, Agent, or Firm* — JCIPRNET

(57) ABSTRACT

An illumination lens consists of a first lens and a second lens that are arranged in this order from a light source side toward an irradiation target side. The surface of the first lens close to the light source side and the surface of the first lens close to the irradiation target side are spherical convex surfaces, and the surface of the second lens close to the light source side is a spherical convex surface. Conditional expression determined in advance about the radii of curvature of the surfaces of the first and second lenses is satisfied.

9 Claims, 6 Drawing Sheets

EXAMPLE 2

(56) References Cited

U.S. PATENT DOCUMENTS

| | | |
|---|---|---|
| 9,211,054 B2 * | 12/2015 | Takato .................... A61B 1/07 |
| 10,441,148 B2 | 10/2019 | Inoue |
| 2009/0287057 A1 | 11/2009 | Murata et al. |
| 2018/0333047 A1 * | 11/2018 | Inoue ................ A61B 1/00096 |

FOREIGN PATENT DOCUMENTS

| | | | |
|---|---|---|---|
| CN | 103562770 | | 2/2014 |
| CN | 108957600 | | 12/2018 |
| JP | H08-320440 | * | 12/1996 |
| JP | 2994229 | | 12/1999 |
| JP | 2005345787 A | * | 12/2005 |
| JP | 4874032 | | 2/2012 |
| JP | 2018194746 | | 12/2018 |

\* cited by examiner

EXAMPLE 1

EXAMPLE 1

EXAMPLE 2

EXAMPLE 2

EXAMPLE 3

EXAMPLE 3

ILLUMINATION LENS, ILLUMINATION OPTICAL SYSTEM, AND ENDOSCOPE

CROSS-REFERENCE TO RELATED APPLICATIONS

The present application claims priority under 35 U.S.C. § 119 to Japanese Patent Application No. 2019-034991, filed on Feb. 27, 2019. The above application is hereby expressly incorporated by reference, in its entirety, into the present application.

BACKGROUND OF THE INVENTION

1. Field of the Invention

The present disclosure relates to an illumination lens, an illumination optical system, and an endoscope.

2. Description of the Related Art

In the related art, an illumination optical system used to illuminate an object to be examined is disposed at the distal end portion of an insertion part of an endoscope. Each of JP4874032B, JP2994229B, and JP2018-194746A disclose an illumination lens consisting of two positive lenses that can be applied to the illumination optical system.

SUMMARY OF THE INVENTION

As a reduction in the size and cost of the distal end portion of an endoscope proceeds, there is also a demand for a reduction in the size and cost of an illumination lens of the endoscope. Accordingly, the achievement of configuration where the number of lenses is small and good light distribution characteristics is required.

Since an endoscope has a wide-angle observation field of view, an illumination lens of the endoscope also requires light distribution characteristics having a wide angle and high uniformity. Since heat is generated in a case where illumination light locally concentrates, light distribution characteristics need to be considered so that the generation of heat is suppressed. To meet the above-mentioned demand, it is preferable that the dispersion of rays emitted from the illumination lens to an irradiation target side is large.

Since the dispersion of rays emitted from the illumination lens to the irradiation target side is small in the illumination lenses disclosed in JP4874032B, JP2994229B, and JP2018-194746A, it is desired that the configuration of the lenses are optimized to further increase the dispersion of rays.

The disclosure has been made in consideration of the above-mentioned circumstances, and an object of the disclosure is to provide an illumination lens that consists of two lenses, has a wide light distribution angle, and has large dispersion of rays on an irradiation target side, an illumination optical system comprising the illumination lens, and an endoscope comprising the illumination lens.

An illumination lens according to a first aspect of the disclosure is an illumination lens used for an illumination optical system of an endoscope, and consists of a first lens and a second lens that are arranged in this order from a light source side toward an irradiation target side. A surface of the first lens close to the light source side and a surface of the first lens close to the irradiation target side are spherical convex surfaces, and a surface of the second lens close to the light source side is a spherical convex surface. In a case where a radius of curvature of the surface of the first lens close to the light source side is denoted by Rf1, a radius of curvature of the surface of the first lens close to the irradiation target side is denoted by Rr1, and a radius of curvature of the surface of the second lens close to the light source side is denoted by Rf2, Conditional expression (1) is satisfied.

$$0.6 < \left| \frac{Rr1 + Rf1}{Rr1 - Rf1} \times \frac{Rf1}{Rf2} \right| < 6 \quad (1)$$

It is preferable that Conditional expression (1-1) is satisfied in the illumination lens according to the first aspect.

$$0.65 < \left| \frac{Rr1 + Rf1}{Rr1 - Rf1} \times \frac{Rf1}{Rf2} \right| < 3 \quad (1-1)$$

An illumination lens according to a second aspect of the disclosure is an illumination lens used for an illumination optical system of an endoscope, and consists of a first lens and a second lens that are arranged in this order from a light source side toward an irradiation target side. A surface of the first lens close to the light source side and a surface of the first lens close to the irradiation target side are spherical convex surfaces, and a surface of the second lens close to the light source side is a spherical convex surface. In a case where a radius of curvature of the surface of the first lens close to the light source side is denoted by Rf1, a radius of curvature of the surface of the first lens close to the irradiation target side is denoted by Rr1, and a radius of curvature of the surface of the second lens close to the light source side is denoted by Rf2, Conditional expression (2) is satisfied.

$$1.2 < \frac{Rf2 + Rf1}{Rf2 - Rf1} \times \frac{Rf2 + Rr1}{Rf2 - Rr1} < 8 \quad (2)$$

It is preferable that Conditional expression (2-1) is satisfied in the illumination lens according to the second aspect.

$$1.5 < \frac{Rf2 + Rf1}{Rf2 - Rf1} \times \frac{Rf2 + Rr1}{Rf2 - Rr1} < 3.5 \quad (2-1)$$

Hereinafter, the illumination lenses according to the first and second aspects of the disclosure will be generically referred to as the illumination lens according to the aspect of the disclosure. In a case where a thickness of the second lens on an optical axis is denoted by t2, a distance on the optical axis between the surface of the first lens close to the light source side and a surface of the second lens close to the irradiation target side is denoted by TL, a focal length of the first lens is denoted by f1, and a focal length of the second lens is denoted by f2, it is preferable that the illumination lens according to the aspect of the disclosure satisfies Conditional expression (3) and it is more preferable that the illumination lens according to the aspect of the disclosure satisfies Conditional expression (3-1).

$$0.6 < (t2/TL) \times (f1/f2) < 6 \quad (3)$$

$$0.65 < (t2/TL) \times (f1/f2) < 3 \quad (3-1)$$

In a case where a focal length of the illumination lens is denoted by f, a thickness of the first lens on an optical axis is denoted by t1, and a distance on the optical axis between the surface of the first lens close to the light source side and a surface of the second lens close to the irradiation target side is denoted by TL, it is preferable that the illumination lens according to the aspect of the disclosure satisfies Conditional expression (4) and it is more preferable that the illumination lens according to the aspect of the disclosure satisfies Conditional expression (4-1).

$$0.02 < |(f/Rr1) \times (t1/TL)| < 0.28 \quad (4)$$

$$0.05 < |(f/Rr1) \times (f1/TL)| < 0.25 \quad (4\text{-}1)$$

In a case where a refractive index of the first lens with respect to a d line is denoted by N1 and a refractive index of the second lens with respect to the d line is denoted by N2, it is preferable that the illumination lens according to the aspect of the disclosure satisfies Conditional expression (5) and it is more preferable that the illumination lens according to the aspect of the disclosure satisfies Conditional expression (5-1).

$$3.6 < N1 \times N2 < 9 \quad (5)$$

$$3.7 < N1 \times N2 < 7 \quad (5\text{-}1)$$

It is preferable that a surface of the second lens close to the irradiation target side is a flat surface in the illumination lens according to the aspect of the disclosure.

The illumination lens according to the aspect of the disclosure may be adapted so that light emitted from an optical fiber is incident on the illumination lens.

An illumination optical system according to another aspect of the disclosure comprises the illumination lens according to the aspect of the disclosure.

An endoscope according to still another aspect of the disclosure comprises the illumination lens according to the aspect of the disclosure.

"Consisting of" and "consist of" in this specification may intend to include a lens substantially not having focal power; optical elements other than a lens, such as a stop, a filter, and a cover glass; a lens flange; a lens barrel; and the like other than described components.

In this specification, "lens having positive focal power" and "positive lens" are synonymous with each other. "Single lens" means one lens that is not cemented. A compound aspherical lens (a lens of which a spherical lens and an aspherical film formed on the spherical lens are integrated and which functions as one aspherical lens as a whole) is treated as one lens without being regarded as a cemented lens.

In this specification, the sign of focal power of a lens, the radius of curvature of the surface of a lens, and the shape of the surface of a lens are considered in a paraxial region unless otherwise specified. The same applies to an aspherical lens. The sign of the radius of curvature of a surface having a convex shape toward an object side is positive and the sign of the radius of curvature of a surface having a convex shape toward an image side is negative.

In this specification, a "focal length" used in Conditional expressions is a paraxial focal length. "TL" used in Conditional expressions is a geometric distance. Values used in Conditional expressions are values that are obtained in a case where the d line (of which the wavelength is 587.56 nm (nanometer)) is used as a reference.

According to the disclosure, it is possible to provide an illumination lens that consists of two lenses, has a wide light distribution angle, and has large dispersion of rays on an irradiation target side, an illumination optical system comprising the illumination lens, and an endoscope comprising the illumination lens.

DESCRIPTION OF THE PREFERRED EMBODIMENTS

Figure 1:
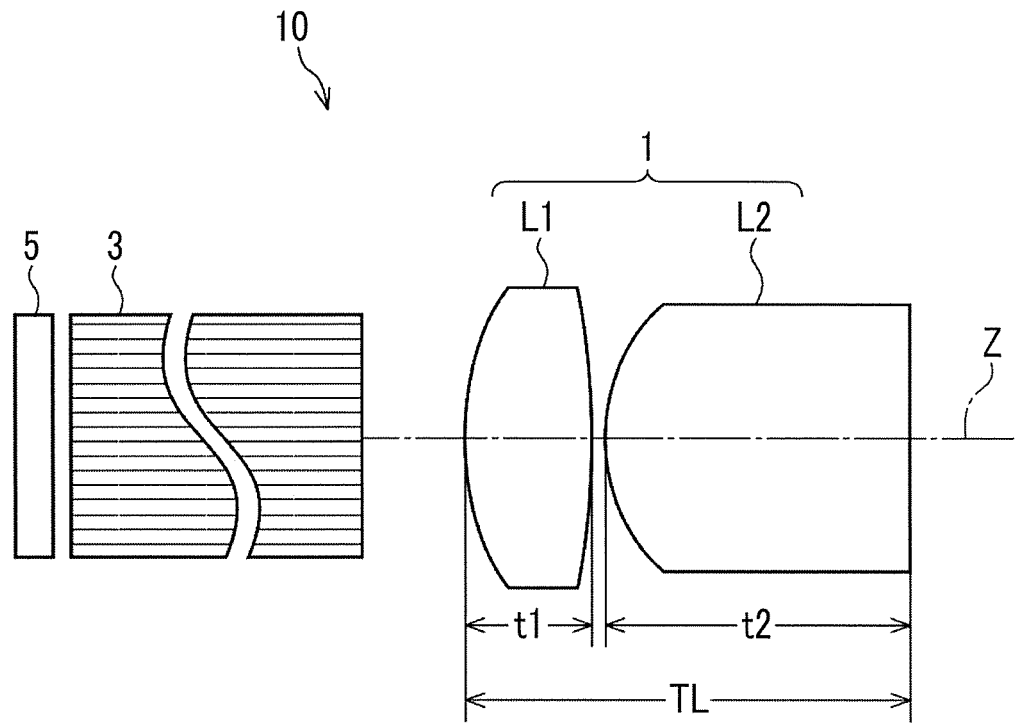
FIG. 1 is a cross-sectional view showing the configuration of an illumination optical system according to an embodiment of the disclosure.

Embodiments of the disclosure will be described in detail below with reference to the drawings. FIG. 1 is a cross-sectional view showing the configuration of an illumination optical system 10 according to an embodiment of the disclosure. The illumination optical system 10 is an optical system used for an endoscope, and comprises an illumination lens 1 according to an embodiment of the disclosure. The illumination lens 1 shown in FIG. 1 corresponds to Example 1 to be described later. Further, the illumination optical system 10 comprises a light source 5 and a light guide 3. The light guide 3 is formed of bundled fibers that are a bundle of a plurality of optical fibers. A member for guiding light may be provided between the light source 5 and the light guide 3.

In FIG. 1, a left side is a light source side and a right side is an irradiation target side.

Light emitted from the light source 5 is incident on the illumination lens 1 through the light guide 3, and is emitted from the illumination lens 1 to form illumination light. In a case where the illumination lens 1 is disposed at the distal end portion of an insertion part of an endoscope, the illumination light illuminates an irradiation target (not shown) that is an object to be observed.

The illumination optical system according to the embodiment of the disclosure is not limited to the configuration shown in FIG. 1. For example, as in an illumination optical system 20 shown in FIG. 2, light emitted from a light source 15 may be incident on an illumination lens 1 without the use of the light guide 3. Further, a plane light source may be used as the light source 5 and the light source 15.

In the configuration shown in FIG. 1, the illumination lens 1 consists of two lenses, that is, a first lens L1 and a second lens L2 arranged along an optical axis Z in this order from the light source side toward the irradiation target side. The surface of the first lens L1 close to the light source side and the surface thereof close to the irradiation target side are spherical convex surfaces. That is, the first lens L1 is a spherical lens having both convex surfaces. The surface of the second lens L2 close to the light source side is a spherical convex surface. In a case where the number of lenses of the illumination lens 1 is set to two and at least three surfaces are formed of spherical surfaces, it is advantageous in reducing cost.

The surfaces of the second lens L2 close to the irradiation target side may be Ruined of a flat surface. In a case where the illumination lens 1 is disposed at the distal end portion of an insertion part of an endoscope, there is a concern that the surface of the second lens L2 close to the irradiation target side may be exposed to body fluid, a washing solution, oil and fat, and the like. In a case where the surface of the second lens L2 close to the irradiation target side is formed of a flat surface, it is difficult for the body fluid, the washing solution, oil and fat, and the like to adhere to the flat surface of the second lens L2 or it is easy to wash the flat surface of the second lens L2 even if the body fluid, the washing solution, oil and fat, and the like adhere to the flat surface of the second lens L2. Accordingly, it is possible to contribute to the suppression of the generation of heat from the distal end portion.

In a case where the radius of curvature of the surface of the first lens L1 close to the light source side is denoted by Rf1, the radius of curvature of the surface of the first lens L1 close to the irradiation target side is denoted by Rr1, and the radius of curvature of the surface of the second lens L2 close to the light source side is denoted by Rf2, the illumination lens 1 is adapted to satisfy at least one of Conditional expression (1) or Conditional expression (2) to be described below.

$$0.6 < \left| \frac{Rr1 + Rf1}{Rr1 - Rf1} \times \frac{Rf1}{Rf2} \right| < 6 \tag{1}$$

$$1.2 < \frac{Rf2 + Rf1}{Rf2 - Rf1} \times \frac{Rf2 + Rr1}{Rf2 - Rr1} < 8 \tag{2}$$

(Rr1+Rf1)/(Rr1−Rf1) of Conditional expression (1) is the shape factor of the first lens L1. In a case where the shape of the surface of the lens is defined so that (Rr1+Rf1)/(Rr1−Rf1)×Rf1/Rf2 is larger than the lower limit of Conditional expression (1), the lens has a wide light distribution angle and it is advantageous in increasing the dispersion of rays of the illumination light. In a case where the shape of the surface of the lens is defined so that [(Rr1+Rf1)/(Rr1−Rf1)]×(Rf1/Rf2) is smaller than the upper limit of Conditional expression (1), total reflection on the surface of the lens can be suppressed or the blocking of some of off-axis rays can be suppressed. Accordingly, a loss in the amount of light can be suppressed. There is a concern that light, which is incident on the illumination lens 1 and is not emitted as illumination light, may cause heat to be generated. Accordingly, it is possible to contribute to the suppression of the generation of heat by making (Rr1+Rf1)/(Rr1−Rf1)×Rf1/Rf2 be smaller than the upper limit of Conditional expression (1). There is also a case where the blocking of some of off-axis rays can be suppressed by an increase in the outer diameter of the lens, but such a case is contrary to a demand for a reduction in the size of the lens.

(Rf2+Rf1)/(Rf2−Rf1) of Conditional expression (2) is a shape factor about the surface of the first lens L1 close to the light source side and the surface of the second lens L2 close to the light source side. (Rf2+Rr1)/(Rf2−Rr1) of Conditional expression (2) is the shape factor of an air lens formed between the first lens L1 and the second lens L2. In a case where the shape of the surface of the lens is defined so that [(Rf2+Rf1)/(Rf2−Rf1)]×[(Rf2+Rr1)/(Rf2−Rr1)] is larger than the lower limit of Conditional expression (2), the lens has a wide light distribution angle and it is advantageous in increasing the dispersion of rays of the illumination light. In a case where the shape of the surface of the lens is defined so that [(Rf2+Rf1)/(Rf2−Rf1)]×[(Rf2+Rr1)/(Rf2−Rr1)] is smaller than the upper limit of Conditional expression (2), total reflection on the surface of the lens can be suppressed or the blocking of some of off-axis rays can be suppressed. Like the effects of the upper limit of Conditional expression (1), it is possible to contribute to the suppression of the generation of heat while reducing the size of the lens by making [(Rf2+Rf1)/(Rf2−Rf1)]×[(Rf2+Rr1)/(Rf2−Rr1)] be smaller than the upper limit of Conditional expression (2).

In a case where the illumination lens 1 satisfies at least one of Conditional expression (1-1) or Conditional expression (2-1), better characteristics can be obtained.

$$0.65 < \left| \frac{Rr1 + Rf1}{Rr1 - Rf1} \times \frac{Rf1}{Rf2} \right| < 3 \tag{1-1}$$

$$1.5 < \frac{Rf2 + Rf1}{Rf2 - Rf1} \times \frac{Rf2 + Rr1}{Rf2 - Rr1} < 3.5 \tag{2-1}$$

Figure 3:
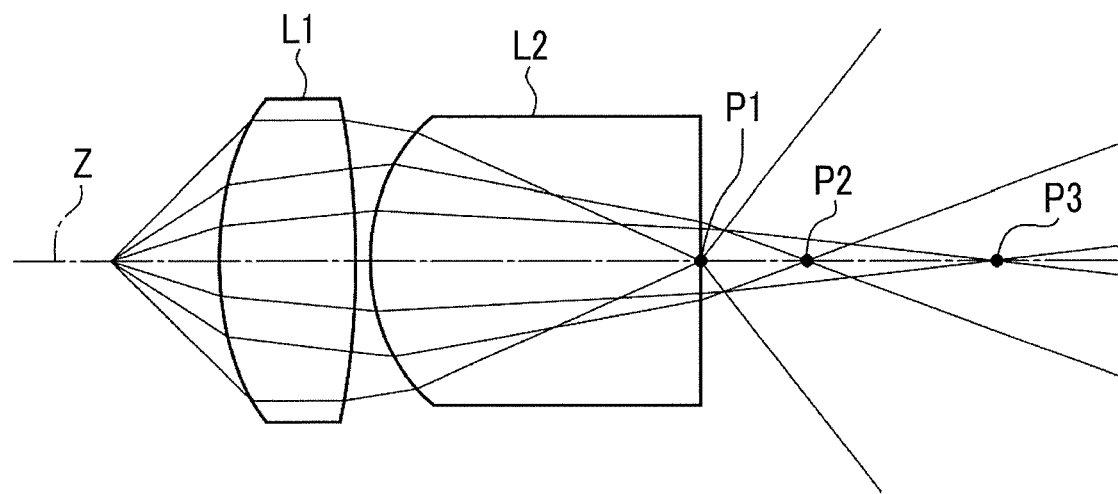
FIG. 3 is a diagram showing the state of rays in a case where a plurality of rays emitted from one point positioned on an optical axis are made to be incident on an illumination lens of Example 1 of the disclosure.

FIG. 3 shows the state of rays in a case where six rays emitted from one point positioned on the optical axis of the emission end face of the light guide 3 are made to be incident on the illumination lens 1 shown in FIG. 1. The light guide 3 is not shown in FIG. 3. The angles of these six rays with respect to the optical axis Z are different from each other. With regard to intersections between the rays on the irradiation target side, an intersection P1 between two rays emitted at the largest angle with respect to the optical axis Z, an intersection P2 between two rays emitted at the second largest angle with respect to the optical axis Z, and an intersection P3 between two rays emitted at the third largest angle with respect to the optical axis Z are shown as black points in FIG. 3. Since the intersections P1, P2, and P3 are positioned to be away from each other without being close to each other, it is found that the rays are significantly dispersed.

Figure 4:
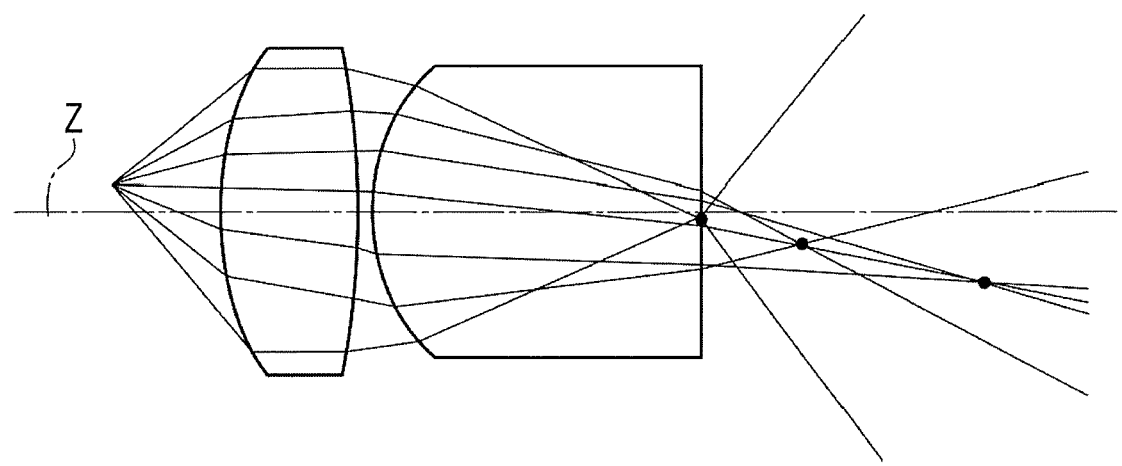
FIG. 4 is a diagram showing the state of rays in a case where a plurality of rays emitted from one point not positioned on the optical axis are made to be incident on the illumination lens of Example 1 of the disclosure.

FIG. 4 shows the state of rays in a case where seven rays emitted from one point not positioned on the optical axis of the emission end face of the light guide 3 are made to be incident on the illumination lens 1 shown in FIG. 1. The light guide 3 is not shown in FIG. 4. The angles of these seven rays with respect to the optical axis Z are different from each other, and one ray among the seven rays is emitted parallel to the optical axis Z. Since the intersections between the respective rays are positioned on the irradiation target side to be away from each other without being close to each other even in the case shown in FIG. 4, it is found that the rays are significantly dispersed. It is possible to suppress the generation of heat from the distal end portion by increasing the dispersion of rays on the irradiation target side.

Further, since the dispersion of rays is increased, the formation of the image of the emission end face of the light guide 3 on the surface of an irradiation target by the illumination lens 1 can be suppressed. Since gaps from which light is not emitted and which are positioned between a clad and fibers and cores emitting light are arranged on the emission end face of the light guide 3 formed of bundled fibers so as to be flush with each other, the emission end face includes dark portions and bright portions. In a case where the image of the emission end face of the light guide 3 is formed on the surface of the irradiation target, the pattern of the dark portions and the bright portions is projected onto the surface of the irradiation target. In a case where this projected image is clear, projected image interferes with observation. In a case where the dispersion of rays on the irradiation target side is increased as in this embodiment, the generation of the projected image of the pattern of the dark portions and the bright portions on the surface of the irradiation target can be suppressed. Accordingly, a case where a combination of the illumination lens 1 and the light guide 3 formed of bundled fibers is used is particularly effective.

Figure 10:
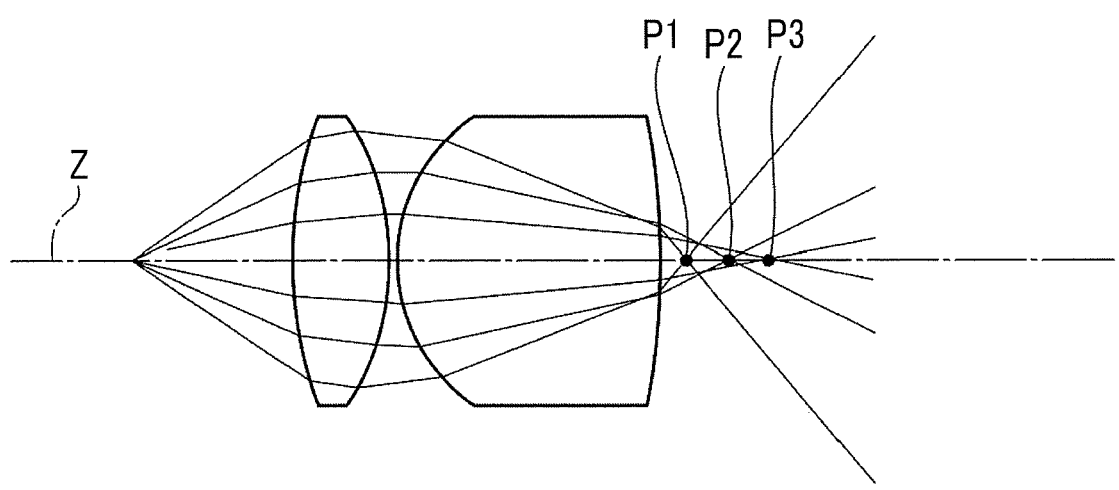
FIG. 10 is a diagram showing the state of rays in a case where a plurality of rays emitted from one point positioned on an optical axis are made to be incident on an illumination lens of Comparative example.

FIG. 10 shows the state of rays in a case where six rays emitted from one point positioned on the optical axis of the emission end face of the light guide 3 are made to be incident on an endoscope illumination optical system of Example 1 of JP4874032B as Comparative example as in FIG. 3. Likewise, an intersection P1 between two rays emitted at the largest angle with respect to the optical axis Z, an intersection P2 between two rays emitted at the second largest angle with respect to the optical axis Z, and an intersection P3 between two rays emitted at the third largest angle with respect to the optical axis Z are shown as black points even in FIG. 10. Since the intersections P1, P2, and P3 are close to each other in Comparative example shown in FIG. 10, it is found that the rays are less dispersed.

Figure 2:
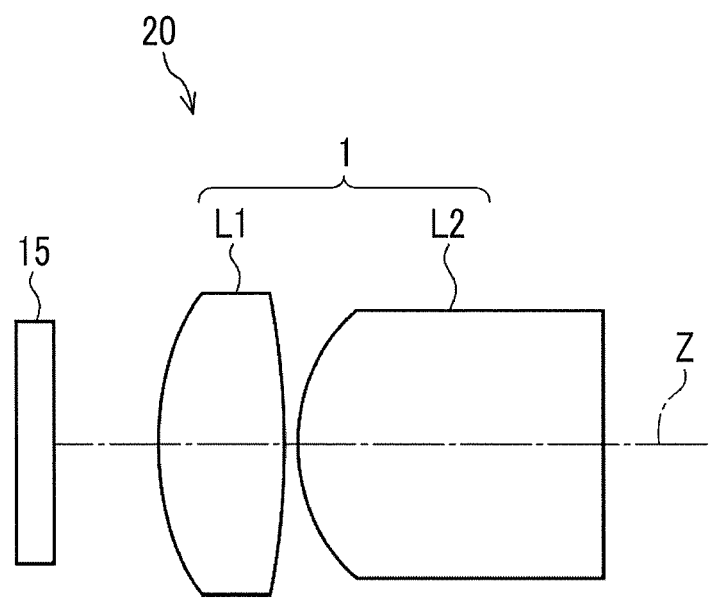
FIG. 2 is a cross-sectional view showing the configuration of an illumination optical system according to another embodiment of the disclosure.

Rays emitted from the emission end face of the light guide 3 have been described in the description made with reference to FIGS. 3, 4, and 10, but configuration which is shown in FIG. 2 in which the emission end face of the light guide 3 of FIG. 1 is replaced with the emission face of the light source 15 of FIG. 2 can also be considered in the same manner as described above. The same applies to Examples to be described later.

It is preferable that the illumination lens 1 according to the embodiment of the disclosure further includes configuration to be described below. In a case where the thickness of the second lens L2 on the optical axis is denoted by t2, a distance on the optical axis between the surface of the first lens L1 close to the light source side and the surface of the second lens L2 close to the irradiation target side is denoted by TL, the focal length of the first lens L1 id denoted by f1, and the focal length of the second lens L2 is denoted by f2, it is preferable that Conditional expression (3) is satisfied. In a case where (t2/TL)×(f1/f2) is made to be larger than the lower limit of Conditional expression (3), it is advantageous in obtaining wide-angle light distribution characteristics. In a case where (t2/TL)×(f1/f2) is made to be smaller than the upper limit of Conditional expression (3), total reflection on the surface of the lens can be suppressed or the blocking of some of off-axis rays can be suppressed. Further, since an increase in the thickness of the second lens L2 on the optical axis can be suppressed in a case where (t2/TL)×(f1/f2) is made to be smaller than the upper limit of Conditional expression (3), a reduction in the amount of light passing through the illumination lens 1 can be suppressed. Accordingly, the generation of heat in the illumination lens 1 can be suppressed. In a case where Conditional expression (3-1) is satisfied, better characteristics can be obtained.

$$0.6 < (t2/TL) \times (f1/f2) < 6 \tag{3}$$

$$0.65 < (t2/TL) \times (f1/f2) < 3 \tag{3-1}$$

Further, in a case the focal length of the illumination lens 1 is denoted by f, the thickness of the first lens L1 on the optical axis is denoted by t1, and a distance on the optical axis between the surface of the first lens L1 close to the light source side and the surface of the second lens L2 close to the irradiation target side is denoted by TL, it is preferable that Conditional expression (4) is satisfied. Since the focal power of the surface of the first lens L1 close to the irradiation target side is not excessively low in a case where (f/Rr1)×(t1/TL) is made to be larger than the lower limit of Conditional expression (4), it is advantageous in reducing a diameter. In a case where |(f/Rr1)×(t1/TL)| is made to be smaller than the upper limit of Conditional expression (4), total reflection on the surface of the lens can be suppressed or the blocking of some of off-axis rays can be suppressed. Further, since an increase in the thickness of the first lens L1 on the optical axis can be suppressed in a case where |(f/Rr1)×(t1/TL)| is made to be smaller than the upper limit of Conditional expression (4), a reduction in the amount of light passing through the illumination lens 1 can be suppressed. Accordingly, the generation of heat in the illumination lens 1 can be suppressed. In a case where Conditional expression (4-1) is satisfied, better characteristics can be obtained.

$$0.02 < |(f/Rr1) \times (t1/TL)| < 0.28 \tag{4}$$

$$0.05 < |(f/Rr1) \times (f1/TL)| < 0.25 \tag{4-1}$$

Furthermore, in a case where the refractive index of the first lens L1 with respect to the d line is denoted by N1 and the refractive index of the second lens L2 with respect to the d line is denoted by N2, it is preferable that Conditional expression (5) is satisfied. In a case where N1×N2 is made to be larger than the lower limit of Conditional expression (5), it is advantageous in obtaining wide-angled light distribution characteristics. Since the illumination lens can be made without using a rare lens material in a case where N1×N2 is made to be smaller than the upper limit of Conditional expression (5), it is possible to avoid a significant increase in cost. In a case where Conditional expression (5-1) is satisfied, better characteristics can be obtained.

$$3.6 < N1 \times N2 < 9 \tag{5}$$

$$3.7 < N1 \times N2 < 7 \tag{5-1}$$

Since the above-mentioned preferable configuration and possible configuration can be randomly combined, it is preferable that the above-mentioned preferable configuration and possible configuration are appropriately selectively employed according to specifications to be required. According to the embodiment of the disclosure, it is possible to realize an illumination lens that can be reduced in size by suppressing the number of lens to two, has a wide light distribution angle, and has large dispersion of rays on the irradiation target side.

Next, numerical examples of the illumination lens according to the embodiment of the disclosure will be described.

Example 1

Since the configuration of an illumination lens of Example 1 is shown in FIG. 1 and the configuration thereof and an illustrating method therefor are as described above, the repeated description thereof will be partially omitted here. The illumination lens of Example 1 consists of a first lens L1 having positive focal power and a second lens L2 having positive focal power that are arranged in this order from the light source side toward the irradiation target side. The first lens L1 is a spherical lens having both convex surfaces. The surface of the second lens L2 close to the light source side is a spherical convex surface, and the surface thereof close to the irradiation target side is a flat surface. Each of the first lens L1 and the second lens L2 is a single lens. The overview of the illumination lens of Example 1 has been described above.

The basic lens data of the illumination lens of Example 1 are shown in Table 1, and the specifications thereof are shown in Table 2. In Table 1, surface numbers that are obtained in a case where the surface closest to the light source side is set as a first surface and the surface number is increased toward the irradiation target side one by one are written in the column of Sn, the radii of curvature of the respective surfaces are written in the column of R, and a surface interval on an optical axis between each surface and a surface, which is positioned on the irradiation target side of each surface so as to be adjacent to each surface, is written in the column of D. Further, the refractive indexes of the respective lenses with respect to the d line are written in the column of Nd, and the Abbe's numbers of the respective lenses with respect to the d line are written in the column of vd. In Table 1, the sign of the radius of curvature of a surface having a convex shape toward the light source side is positive and the sign of the radius of curvature of a surface having a convex shape toward the irradiation target side is negative.

The focal length f of the illumination lens, the diameter LGDia of the emission end face of the light guide 3 disposed on the light source side of the illumination lens, and an interval d0 on the optical axis between the light guide 3 and the illumination lens are shown in Table 2 with respect to the d line. Numerical values, which are rounded off to a predetermined place, are written in Table 1 and Table 2.

TABLE 1

| Example 1 | | | | |
|---|---|---|---|---|
| Sn | R | D | Nd | vd |
| 1 | 2.2901 | 1.0200 | 2.05090 | 26.94 |
| 2 | −6.3702 | 0.1049 | | |
| 3 | 1.5157 | 2.4423 | 1.88299 | 40.78 |
| 4 | ∞ | | | |

TABLE 2

| Example 1 | |
|---|---|
| f | 1.00 |
| LGDia | ϕ1.94 |
| d 0 | 0.8088 |

The states of rays in a case where a plurality of rays emitted from one point positioned on the emission end face of the light guide are made to be incident on the illumination lens of Example 1 are shown in FIGS. 3 and 4. Since the description thereof is as described above, the repeated description will be partially omitted here.

Since the symbols, meanings, writing methods, and illustrating methods for data about Example 1 are the same as those of other examples to be described below unless otherwise specified, the repeated description thereof will be omitted below.

Example 2

An illumination lens of Example 2 has the same configuration as the overview of the illumination lens of Example 1. A combination of the illumination lens of Example 2 and the light guide can also be used as in the case of the illumination lens of Example 1. The basic lens data of the illumination lens of Example 2 are shown in Table 3, and the specifications thereof are shown in Table 4.

TABLE 3

| Example 2 | | | | |
|---|---|---|---|---|
| Sn | R | D | Nd | vd |
| 1 | 2.4059 | 1.0558 | 2.05090 | 26.94 |
| 2 | −14.0864 | 0.0985 | | |
| 3 | 1.4388 | 2.1821 | 2.00100 | 29.13 |
| 4 | ∞ | | | |

TABLE 4

| Example 2 | |
|---|---|
| f | 1.00 |
| LGDia | ϕ1.90 |
| d 0 | 0.7602 |

Figure 5:
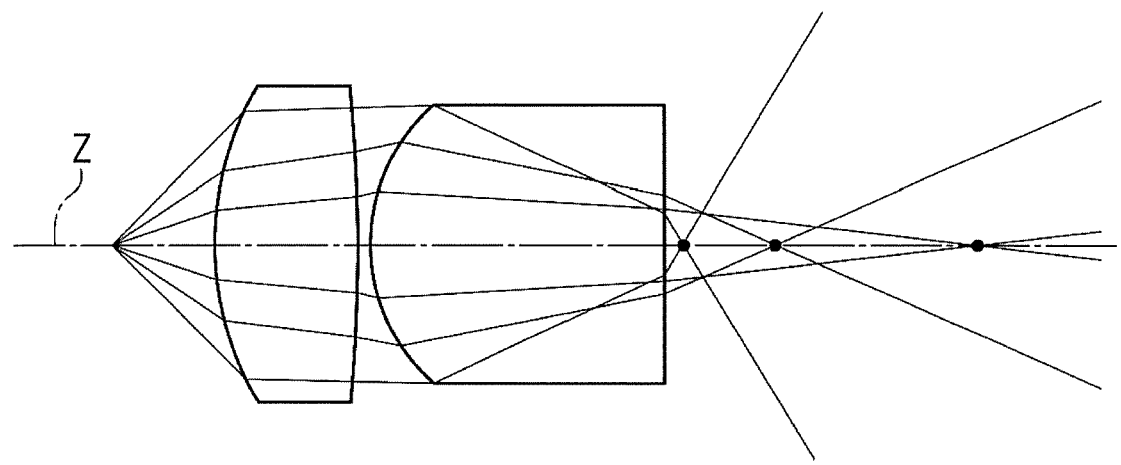
FIG. 5 is a diagram showing the state of rays in a case where a plurality of rays emitted from one point positioned on an optical axis are made to be incident on an illumination lens of Example 2 of the disclosure.
Figure 6:
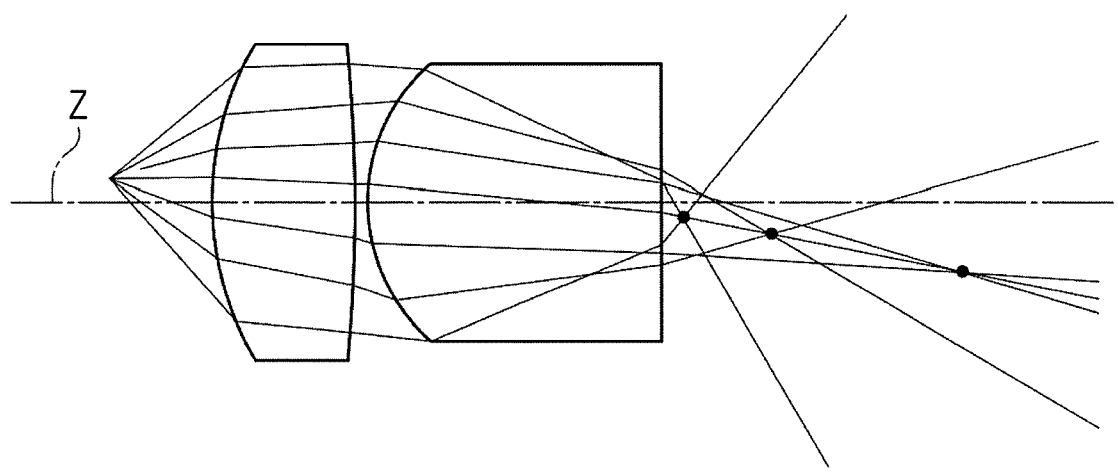
FIG. 6 is a diagram showing the state of rays in a case where a plurality of rays emitted from one point not positioned on the optical axis are made to be incident on the illumination lens of Example 2 of the disclosure.

The state of rays in a case where a plurality of rays emitted from one point positioned on the optical axis of the emission end face of the light guide are made to be incident on the illumination lens of Example 2 and the state of rays in a case where a plurality of rays emitted from one point not positioned on the optical axis of the emission end face of the light guide are made to be incident on the illumination lens of Example 2 are shown in FIGS. 5 and 6, respectively.

Example 3

An illumination lens of Example 3 has the same configuration as the overview of the illumination lens of Example 1. A combination of the illumination lens of Example 3 and the light guide 3 can also be used as in the case of the illumination lens of Example 1. The basic lens data of the illumination lens of Example 3 are shown in Table 5, and the specifications thereof are shown in Table 6.

TABLE 5

| Example 3 | | | | |
|---|---|---|---|---|
| Sn | R | D | Nd | vd |
| 1 | 2.4776 | 1.2374 | 2.00100 | 29.13 |
| 2 | −5.2597 | 0.0996 | | |
| 3 | 1.3555 | 1.8490 | 1.88299 | 40.78 |
| 4 | ∞ | | | |

TABLE 6

| Example 3 | |
|---|---|
| f | 1.00 |
| LGDia | φ1.85 |
| d 0 | 0.7112 |

Figure 7:
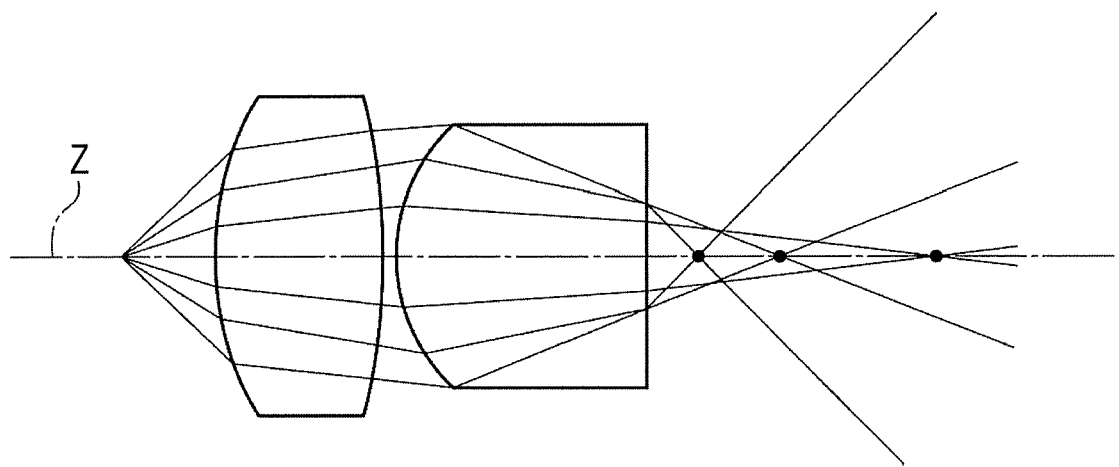
FIG. 7 is a diagram showing the state of rays in a case where a plurality of rays emitted from one point positioned on an optical axis are made to be incident on an illumination lens of Example 3 of the disclosure.
Figure 8:
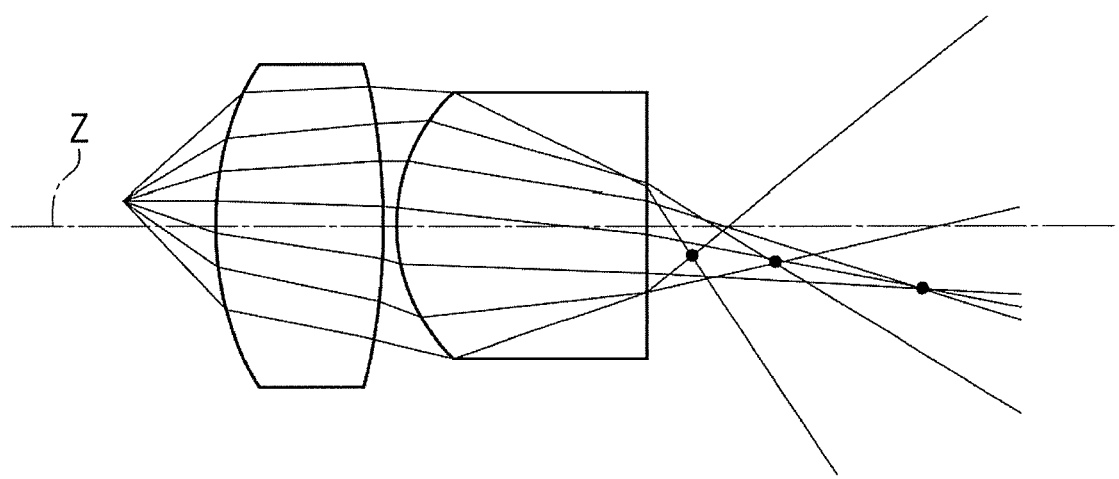
FIG. 8 is a diagram showing the state of rays in a case where a plurality of rays emitted from one point not positioned on the optical axis are made to be incident on the illumination lens of Example 3 of the disclosure.

The state of rays in a case where a plurality of rays emitted from one point positioned on the optical axis of the emission end face of the light guide are made to be incident on the illumination lens of Example 3 and the state of rays in a case where a plurality of rays emitted from one point not positioned on the optical axis of the emission end face of the light guide are made to be incident on the illumination lens of Example 3 are shown in FIGS. 7 and 8, respectively.

The values of Conditional expressions (1) to (5) corresponding to the illumination lenses of Examples 1 to 3 are shown in Table 7. In Examples 1 to 3, the d line is used as a reference wavelength. Table 7 shows values with respect to the d line.

TABLE 7

| Expression number | | Example 1 | Example 2 | Example 3 |
|---|---|---|---|---|
| (1) | \|S1 × Rf1/Rf2\| | 0.71 | 1.18 | 0.66 |
| (2) | Sa × Sb | 3.03 | 3.24 | 2.02 |
| (3) | (t2/TL) × (f1/f2) | 0.68 | 0.92 | 0.69 |
| (4) | \|(f/Rr1) × (t1/TL)\| | 0.16 | 0.07 | 0.24 |
| (5) | N1 × N2 | 3.86 | 4.10 | 3.77 |

Here.

$S1=(Rr1+Rf1)/(Rr1-Rf1)$ $Sa=(Rf2+Rf1)/(Rf2-Rf1)$ $Sb=(Rf2+Rr1)/(Rf2-Rr1)$

Figure 9:
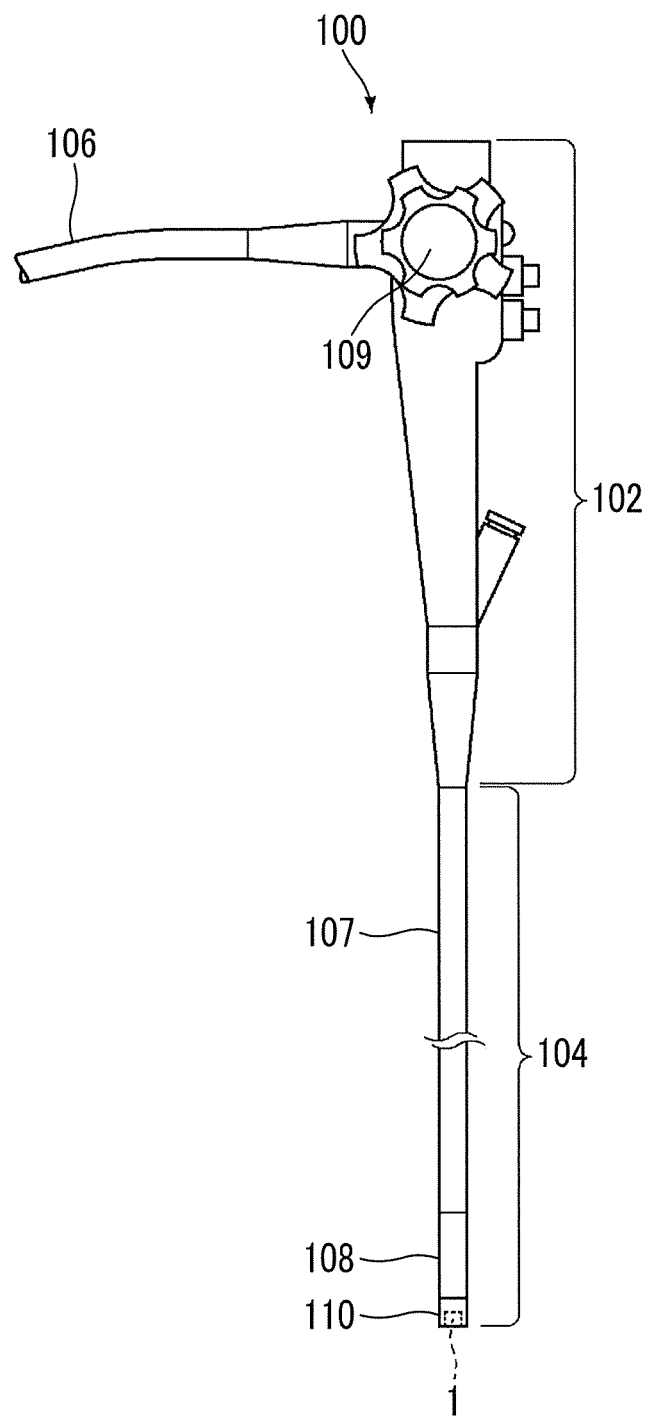
FIG. 9 is a diagram showing the schematic configuration of an endoscope according to an embodiment of the disclosure.

Next, an endoscope according to an embodiment of the disclosure will be described. A diagram showing the schematic configuration of the entire endoscope according to an embodiment of the disclosure is shown in FIG. 9. The endoscope 100 shown in FIG. 9 mainly comprises an operation part 102, an insertion part 104, and a universal cord 106 that is to be connected to a connector part (not shown). A large portion of the insertion part 104 is a soft portion 107 that is bendable in any direction along an insertion path, a bendable portion 108 is connected to the distal end of the soft portion 107, and a distal end portion 110 is connected to the distal end of the bendable portion 108. The bendable portion 108 is provided to allow the distal end portion 110 to face in a desired direction, and can be operated to be bent by the rotational movement of bending operation knobs 109 provided on the operation part 102. The illumination lens 1 according to the embodiment of the disclosure is provided in the distal end of the distal end portion 110. The illumination lens 1 is schematically shown in FIG. 9. Since the endoscope according to the embodiment of the disclosure comprises the illumination lens according to the embodiment of the disclosure, the size of the distal end portion of the insertion part 104 is reduced and the generation of heat is suppressed. Accordingly, it is possible to make an observation using good illumination light with a wide angle.

A technique of the disclosure has been described above using the embodiments and the examples, but the technique of the disclosure may have various modifications without being limited to the embodiments and the examples. For example, the radius of curvature, the surface interval, the refractive index, the Abbe's number, and the like of each lens may have other values without being limited to values shown in the respective numerical examples.

What is claimed is:

1. An illumination optical system of an endoscope, the illumination optical system comprising:
   an illumination lens consisting of a first lens and a second lens that are arranged in this order from a light source side toward an irradiation target side; and
   a point light source configured to emit a plurality of light rays to the illumination lens, wherein angles of the plurality of light rays incident on the illumination lens with respect to an optical axis of the illumination lens are different from each other,
   wherein the illumination lens is configured to directly receive the plurality of light rays from the point light source and cause all of the plurality of light rays to intersect on the irradiation target side at positions outside the second lens,
   wherein a surface of the first lens closest to the light source side and a surface of the first lens closest to the irradiation target side are spherical convex surfaces,
   a surface of the second lens closest to the light source side is a spherical convex surface, and
   in a case where a radius of curvature of the surface of the first lens closest to the light source side is denoted by Rf1, a radius of curvature of the surface of the first lens closest to the irradiation target side is denoted by Rr1, and a radius of curvature of the surface of the second lens closest to the light source side is denoted by Rf2, Conditional expression (1) is satisfied, $$0.6 < \left| \frac{Rr1 + Rf1}{Rr1 - Rf1} \times \frac{Rf1}{Rf2} \right| < 6. \tag{1}$$

2. The illumination optical system according to claim 1, wherein a surface of the second lens closest to the irradiation target side is a flat surface.

3. The illumination optical system according to claim 1, wherein light emitted from an optical fiber is incident on the illumination lens.

4. The illumination optical system according to claim 1, wherein Conditional expression (1-1) is satisfied, $$0.65 < \left| \frac{Rr1 + Rf1}{Rr1 - Rf1} \times \frac{Rf1}{Rf2} \right| < 3. \tag{1-1}$$

5. An endoscope comprising:
   the illumination optical system according to claim 1.

6. The illumination optical system according to claim 1, wherein in a case where a thickness of the second lens on the optical axis is denoted by t2, a distance on the optical axis between the surface of the first lens closest to the light source side and a surface of the second lens closest to the irradiation target side is denoted by TL, a focal length of the first lens is denoted by f1, and a focal length of the second lens is denoted by f2, Conditional expression (3) is satisfied, $$0.6 < (t2/TL) \times (f1/f2) < 6. \tag{3}$$

7. The illumination optical system according to claim 6, wherein Conditional expression (3-1) is satisfied, $$0.65 < (t2/TL) \times (f1/f2) < 3 \qquad (3\text{-}1).$$

8. The illumination optical system according to claim 1, wherein in a case where a refractive index of the first lens with respect to a d line is denoted by N1 and a refractive index of the second lens with respect to the d line is denoted by N2, Conditional expression (5) is satisfied, $$3.6 < N1 \times N2 < 9 \qquad (5).$$

9. The illumination optical system according to claim 8, wherein Conditional expression (5-1) is satisfied, $$3.7 < N1 \times N2 < 7 \qquad (5\text{-}1).$$

* * * * *